United States Patent [19]

Carson

[11] Patent Number: 5,406,684
[45] Date of Patent: Apr. 18, 1995

[54] SANITARY SURGICAL BLADE REMOVAL INSTRUMENT

[76] Inventor: Thomas E. Carson, 1536 Fairway Dr., Camarillo, Calif. 93010

[21] Appl. No.: 89,935

[22] Filed: Jul. 12, 1993

[51] Int. Cl.$^6$ .............................................. B23P 19/04
[52] U.S. Cl. ......................................... 29/239; 29/278
[58] Field of Search ...................... 29/268, 239, 281.1, 29/281.5, 283, 278, 426.5; 206/349, 355, 359

[56] References Cited

U.S. PATENT DOCUMENTS

| | | |
|---|---|---|
| 4,168,777 | 9/1979 | Gaskell . |
| 4,344,532 | 8/1982 | Eldridge . |
| 4,395,807 | 8/1983 | Eldridge . |
| 4,730,376 | 3/1988 | Yamada . |
| 4,746,016 | 5/1988 | Pollack . |
| 4,903,390 | 2/1990 | Vidal . |
| 4,998,334 | 3/1991 | Pemberton . |
| 5,088,173 | 2/1992 | Kromer . |

OTHER PUBLICATIONS

Miltex Hi-Lights "Blade-Safe".

*Primary Examiner*—Robert C. Watson
*Attorney, Agent, or Firm*—Poms, Smith, Lande and Rose

[57] ABSTRACT

A sanitary surgical blade removal instrument for removing a disposable blade from the handle of a surgical tool. The instrument consisting of a piece of sheet metal bent at a C-shaped flexible fold to produce an upper portion and a lower portion which extend generally parallel to one another. The upper and lower portions of the sheet metal form the upper and lower portions of a blade gripping and flexing end and the upper and lower portions of a handle end. To use the blade removal instrument, the surgical tool is inserted into the removal instrument so that the neck of the surgical tool rests within a lower notch in a lower ridge of the lower portion of the removal instrument such that the lower ridge on either side of the lower notch engages the underneath side of the disposable blade. The user squeezes the upper and lower portions of the handle of the removal instrument, keeping his hand at a safe distance from the sharp contaminated blade. The handle of the surgical tool may then be pulled away from the blade while the blade remains securely gripped in the gripping section of the removal instrument. The blade may then be disposed of safely with the hand of the user safely positioned on the handle of the instrument, away from the contaminated sharp blade. Finally, the removal instrument may be sterilized so the removal instrument may be reused.

19 Claims, 2 Drawing Sheets

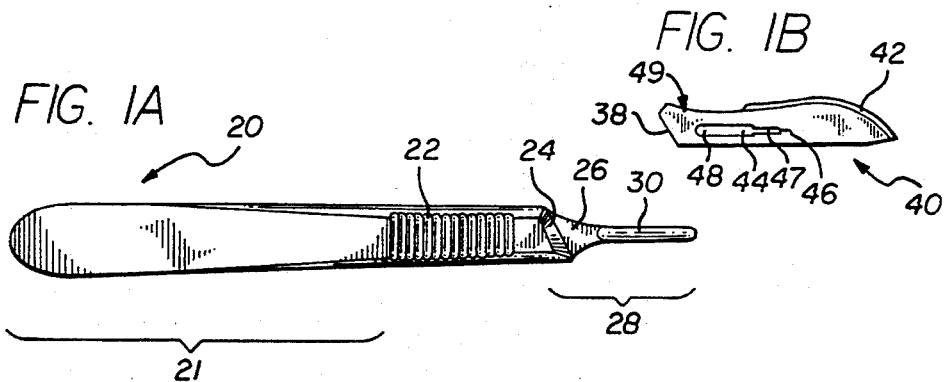
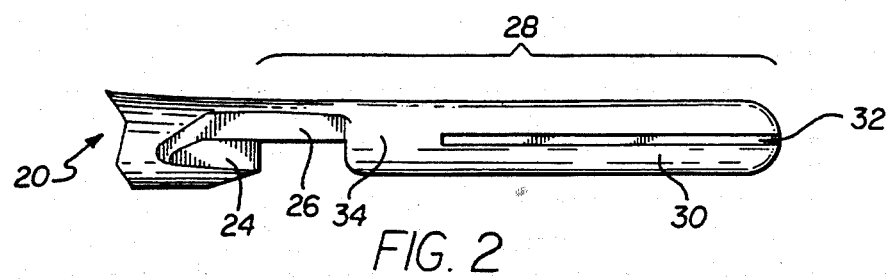
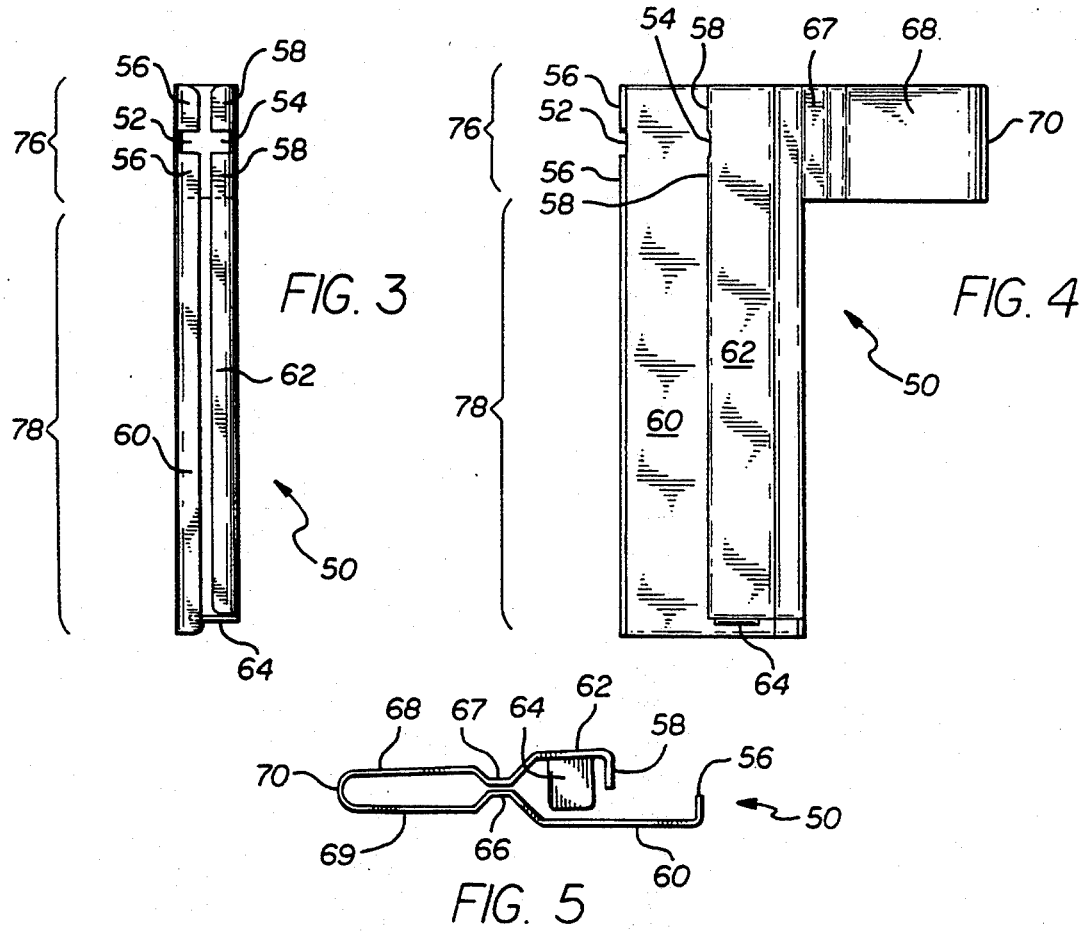

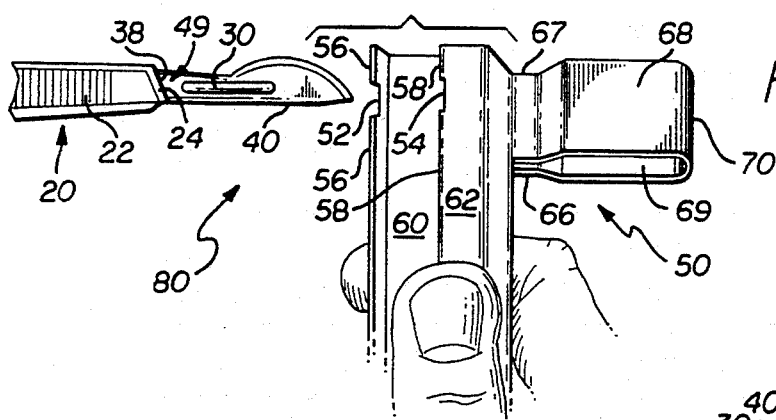
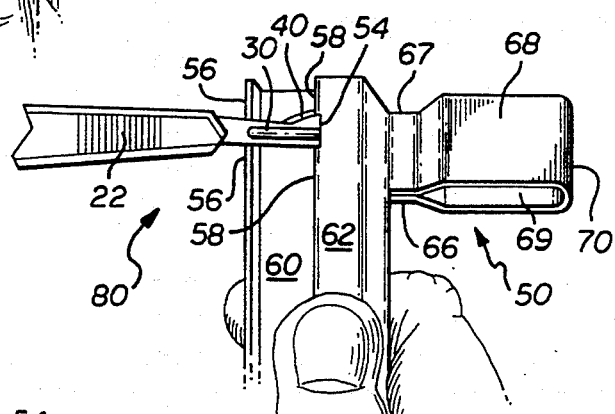
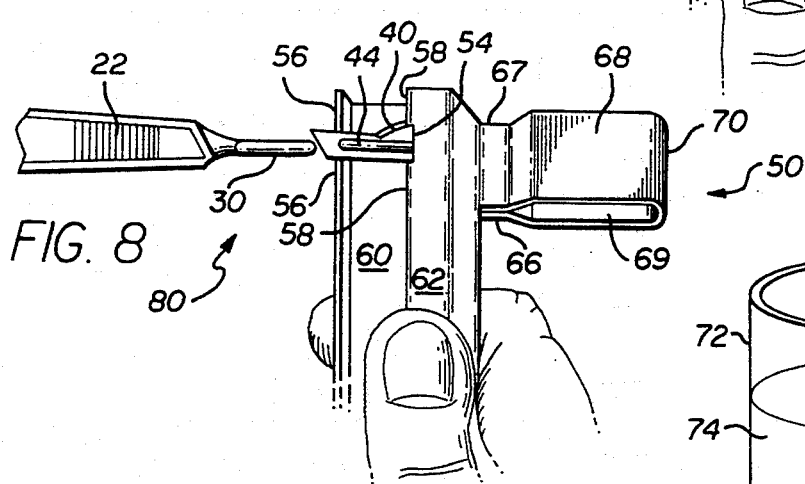
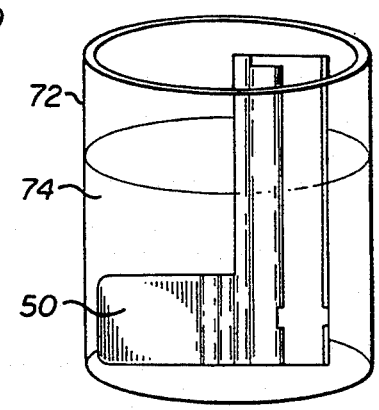
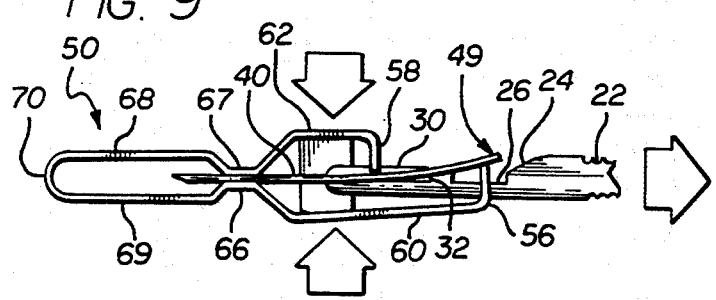

SANITARY SURGICAL BLADE REMOVAL INSTRUMENT

FIELD OF THE INVENTION

This invention relates to an instrument for removing disposable or contaminated blades from the handle of a surgical tool.

BACKGROUND OF THE INVENTION

Surgical tools such as scalpels and knives generally consist of a tool handle and a disposable blade. The present invention is an instrument which safely and sanitarily removes the disposable blade from the tool handle. A handle of a surgical tool generally consists of a long, flat, lower portion, a gripping surface, a shoulder, and a narrowed portion. The narrowed portion consists of a neck and a raised, elongated retaining member. The elongated retaining member usually has a narrow groove on both sides of its upper portion. A disposable blade, which attaches to the tool handle, generally has an elongated slot therein which engages with the elongated retaining member of the tool handle. The slot has three sections, a narrow upper portion, a medium middle portion, and a wide lower portion. The upper and middle portions of the slot are compatible with the grooves on both sides of the upper portion of the retaining member. The blade is secured to the tool handle by sliding the upper, grooved portion of the retaining member through the upper and middle portions of the blade slot. The blade is then flexed so that the wide lower portion of the blade slot flexes over the rear portion of the retaining member (toward the handle). The blade unflexes when the wide lower portion of the slot has passed the rear portion of the raised retaining member. In this unflexed state, the blade lies flat with the neck of the handle with the retaining member protruding through the blade slot, and thus secures the blade to the tool handle.

The tool handle portion of a surgical knife, being relatively costly, is cleaned and sterilized after each use. A blade, however, is relatively inexpensive. In addition, multiple usage dulls a surgical blade. Therefore, the surgical blades are considered disposable. It is important that the contaminated blade be removed in an efficient and safe manner so that personnel does not risk possible cuts or infection from a contaminated blade. After removal, contaminated surgical blades should be disposed of properly.

It is known to remove a surgical blade from a tool handle using forceps. Forceps, however, have several disadvantages. They are not specifically designed for removing surgical blades and, therefore, often fail to remove the blade on the first try. There is also the possibility that during the removal procedure, blood or other material could drip from the contaminated surgical knife. Additionally, because forceps are often hinged, they are generally difficult to sterilize after being used to remove a contaminated blade.

It is also known to use a device which includes a compartment such that when the blade is inserted into the compartment the blade is flexed so that the lower portion of the blade slot flexes over the raised retaining member of the handle. The handle may then be easily separated from the blade. These devices usually retain the contaminated blade in the compartment. Examples of a compartment type of device include U.S. Pat. No. 4,168,777, U.S. Pat. No. 4,395,807, U.S. Pat. No. 4,998,334, U.S. Pat. No. 5,088,173, U.S. Pat. No. 4,746,016, U.S. Pat. No. 4,344,532, U.S. Pat. No. 4,903,390, and U.S. Pat. No. 4,730,376. These compartment devices all contain at least one compartment which can secure at least one blade. As compared with the present invention, these devices are difficult to manufacture. Another problem is the difficulty in sanitizing these devices which often contain small cracks in which contaminated material often remains undetected after sterilization. Because of the difficulty in sanitizing these devices, most are disposable.

It is also known to use a single sheet metal device designed for removing a blade from a handle of a surgical tool. The metal sheet is bent at a C-shaped, flexible fold which separates an upper portion and a lower portion which extend generally parallel to one another. This device would generally contain the following: an edge of the lower portion opposite the fold, angled upward to form a lower ridge which defines a lower notch, the lower ridge on either side of the notch being used to selectively apply pressure to the lower side of the blade on either side of the neck of the tool handle; an upper portion narrower than the lower portion, with the edge of the upper portion opposite the fold angled downward to form an upper ridge which defines an upper notch, the upper ridge on either side of the notch being used to selectively apply pressure to the upper side of the blade on either side of the retaining member of the tool handle; the middle section of both the upper portion and the lower portion bent inward to form a blade gripping section for gripping the blade above the blade slot; and the fold itself which may function as a blade protector for covering the tip of the blade.

To use this sheet metal device for removing a blade, a user may place his fingers and thumb of one hand below the under notch and above the over notch respectively. Using the free hand, the user would generally grip the surgical tool by its handle and insert the blade into the single sheet device. When the user squeezes the upper and lower portions of the single sheet device, the blade gripping section grips the tip of the blade, the upper ridge applies pressure downward on the middle section of the blade, and the under ridge applies pressure upward on the lower end of the blade. These conflicting pressures cause the lower end of the blade to flex upward above the raised retaining member of the tool handle. The user may then pull the handle away from the contaminated blade.

This sheet metal device, because the user's fingers are in close proximity to the contaminated blade, puts the user in danger of coming into contact with dangerous contaminants. Further, as the user loosened his grip so as to allow him to remove the blade from the single sheet device, the blade gripping section opens to permit the contaminated blade to slip out. The contaminated blade, since it is not being held by the blade gripping section, could easily slip and cut the user's hand. This is dangerous as it risks possible cuts and infection from a sharp contaminated blade; and this danger has been increased in recent months by the widespread incidence of AIDS.

Accordingly, principal objects of the present invention are as follows: to provide a means for safe and sanitary removal of contaminated blades from surgical instruments; to provide a removal instrument which is easy and relatively inexpensive to manufacture; to provide a removal instrument which is easy to sanitize; and to provide a removal instrument which may be reused after sanitization.

BRIEF SUMMARY OF THE INVENTION

In accordance with the present invention, a single sheet of metal is bent at a C-shaped, flexible fold to form an upper portion and lower portion which are substantially parallel to each other. The upper and lower portions of the sheet metal form the upper and lower portions of a blade gripping and flexing end and the upper and lower portions of a handle end. The blade gripping and flexing end forms an L-shape with the handle end.

More specifically, the present invention includes the following characteristics: a flexible, C-shaped fold from which extends an upper portion and lower portion of a blade protector for covering the tip of the blade; upper and lower portions of a blade gripping section adjoining the upper and lower portions of the blade protector; an upper handle portion, with the edge opposite the fold angled downward to form an upper ridge which defines an upper notch, the upper ridge on either side of the notch being used to selectively apply pressure to the upper side of the blade on either side of the retaining member of the tool handle; and a lower handle portion, which is wider than the upper handle portion, of which the edge opposite the fold is angled upward to form a lower ridge which defines a lower notch, the lower ridge on either side of the notch being used to selectively apply pressure to the lower side of the blade on either side of the neck of the tool handle.

To use the blade removal instrument, the surgical tool is inserted into and positioned in the removal instrument as follows: the neck of the surgical tool rests within the lower notch of the lower ridge of the removal instrument so that the lower ridge on either side of the lower notch touches the underneath side of the lower portion of a surgical blade; the retaining member on the upper narrowed portion of the surgical tool is directly below the upper notch in the upper ridge of the removal instrument so that the upper ridge on either side of the upper notch is directly above the middle portion of the upper side of the blade; and the uppermost portion of the blade rests between the upper and lower gripping sections.

The user squeezes the upper and lower handles of the removal instrument keeping his hands at a safe distance from the sharp contaminated blade. As the handles of the removal instrument move towards each other, the removal instrument comes into contact with the contaminated blade as follows: the blade gripping section grips the outer portion of the blade; the upper ridge on each side of the upper notch pushes down on the middle section of the blade surrounding the retaining member; and the lower ridge on each side of the lower notch applies pressure to the underneath side of the inner portion of the blade on either side of the neck of the surgical tool handle. As the user applies more pressure, the inner portion of the blade (toward the handle) flexes above the inner portion of the raised retaining member of the tool handle. The tool handle may then be pulled away from the blade while the blade remains securely gripped in the gripping section of the removal instrument.

The removal instrument, and the blade contained therein, may then be positioned over a container appropriate for the disposal of the contaminated blade. The blade is secure and in no danger of slipping out of the removal instrument. Since it is enclosed both above and below by the removal instrument, any contaminants which drip off the blade are caught by the removal instrument. By releasing the handles, the blade may then be allowed to fall into the disposal container. Throughout this process, the hand of the user remains safely on the handle away from the sharp contaminated blade.

The removal instrument may then be placed in a sterilizing container containing a sanitary solution to sterilize the removal instrument so it may be reused. Again, the user's hands and fingers are at a safe distance from the contaminated blade and any other contaminating materials, thereby removing the risk of possible cuts and infection.

The preferred embodiments of the invention may also include the following additional features:

1. a handle stop designed to prevent the upper and lower handles from mating, and located at the outer ends of the handles, so that pressure on the handles actuates the blade flexing action described above;
2. a handle stop fashioned by bending an end portion of the upper handle to the desired distance between the handles;
3. a handle stop fashioned by bending an end portion of the lower handle to the desired distance between the handles;
4. the material from which the removal instrument is constructed is sterilizable; and
5. the material from which the removal instrument is constructed is stainless steel.

The major advantages of the present invention over other blade removal devices include the following: the safety handle which allows the user to use the instrument with his fingers at a distance from the contaminated blade, thus allowing safe and sanitary removal and disposal of contaminated blades; the single sheet metal construction which is cost effective and easy to manufacture; and the ability to reuse the removal instrument after easy sterilization.

Other objects, features and advantages of the present invention will become apparent from a consideration of the following detailed description, and from the accompanying drawings.

BRIEF DESCRIPTION OF THE DRAWINGS

FIG. 1A is a front view of a handle of a standard surgical tool or scalpel;

FIG. 1B is a front view of a blade of a standard surgical tool or scalpel;

FIG. 2 is an enlarged side view of the narrowed front end of a handle of a standard surgical tool;

FIG. 3 is a side view of a sanitary surgical blade removal instrument illustrating the principles of the invention;

FIG. 4 is a front view of a sanitary surgical blade removal instrument;

FIG. 5 is a top view of a sanitary surgical blade removal instrument;

FIG. 6 is a front view illustrating the proper insertion of the standard surgical tool with a removable blade into the sanitary surgical blade removal instrument;

FIG. 7 is a front view illustrating the proper position of the standard surgical tool with a removable blade when the blade is gripped by the sanitary surgical blade removal instrument;

FIG. 8 is a front view illustrating the proper removal of the handle of the standard surgical tools from the blade of the standard surgical tool which is gripped within the sanitary surgical blade removal instrument;

FIG. 9 is a top view of the sanitary surgical blade removal instrument gripping and flexing the blade of a standard surgical tool; and FIG. 10 is a sanitary surgical blade removal instrument in a sanitizing solution.

DETAILED DESCRIPTION OF THE PREFERRED EMBODIMENTS

FIG. 1A shows a surgical tool handle 20 of a standard surgical tool 80 (as shown in FIG. 6) such as a scalpel or knife. For convenience, the left hand ends of the tool handle 20 and blade 40 as shown in FIG. 1A and FIG. 1B will be referred to as the "rear" of these elements, with the right hand ends being the "front"; and the side of the handle facing outward in FIG. 1A and carrying the retaining member 30 will be referred to as the upper side of the tool handle 20. The tool handle 20 may consist of a rear portion 21, a middle grip portion 22, and a front narrowed portion 28. Between the front narrowed portion 28 and the middle grip portion 22 is an angled shoulder 24. The front narrowed portion 28 consists of a narrow neck portion 26 and a raised retaining member 30. FIG. 2 details an enlarged side view of the front narrowed portion 28 of the surgical tool handle 20. This figure further shows the angled shoulder 24, the narrow neck 26, and the raised retaining member 30 of the front narrowed portion 28 of the tool handle 20. Specifically, FIG. 2 shows the groove 32 on the front portion of the raised retaining member 30 and the non-grooved rear portion 34 of the raised retaining member 30.

FIG. 1B shows a standard surgical tool blade 40. A standard surgical tool blade 40 may include at least one cutting edge 42. Also, beyond the rear portion 49 of the surgical blade 40, there is preferably an angled rear edge 38 which adjoins the angled shoulder 24 of the tool handle 20 when the surgical blade 40 is attached to the tool handle 20 (as shown in FIG. 6). In the rear central portion of the surgical blade 40 is a slot 44. The slot 44 includes a narrow front portion 46, a medium middle portion 47, and a wide rear portion 48.

The blade 40 is secured to the tool handle 20 by sliding the front grooved portion 32 of the retaining member 30 through the front and middle portions (46 and 47) of the blade slot 44. The blade 40 is then flexed so that the wide rear slot portion 48 flexes above the non-grooved rear portion 34 of the raised retaining member 30. When the rear slot portion 48 reaches the rear end of the retaining member 30, the blade 40 straightens or unflexes so that the rear portion 49 of the blade 40 rests on the neck 26 of the tool handle 20. In this position the retaining member 30 is completely surrounded by and protrudes through the slot 44 of the blade 40. The blade 40 is thus secured to the handle 20 of the surgical tool 80 (as shown in FIG. 6).

The sanitary surgical blade removal instrument 50 as shown in FIG. 3, FIG. 4, and FIG. 5 is preferably made from a single piece of flexible, sanitizable material such as a metal. For example, stainless steel would be an appropriate metal for the present invention. In the alternative, a flexible, non-porous plastic could be used to construct a sanitizable, flexible removal instrument.

The single sheet of metal is bent at a C-shaped, flexible fold 70 to form an upper portion (62, 67, and 68) and a lower portion (60, 66, and 69) which are substantially parallel to each other. The upper and lower portions of the sheet metal form the upper and lower portions of a blade gripping and flexing end 76 and the upper and lower portions of a handle end 78. The blade gripping and flexing end 76 forms an L-shape with the handle end 78.

As indicated above, the metal sheet from which the removal instrument 50 is preferably constructed is loosely bent into a C-shaped fold 70. This fold 70 preferably functions as a spring so that when the handles (60 and 62) are squeezed together the gripping section (66 and 67) of the gripping and flexing end 76 grips the blade 40 of the surgical tool 80. The fold 70 divides the metal sheet into an upper section (62, 67, and 68) and a lower section (60, 66, and 69).

Adjacent to the fold 70 is the blade protector (68 and 69). The blade protector has an upper portion 68 and a lower portion 69. When the blade 40 is inserted into the removal instrument 50, the blade protector (68 and 69) prevents a user's fingers from getting near the sharp cutting edge 42 of the blade 40 and any contaminated materials which might be on the blade 40. In addition, contaminated materials would drip onto the lower portion 69 of the blade protector (68 and 69) and thereby prevent contamination of floors, tables, or other sanitary surfaces.

Adjacent to the upper and lower blade protectors (68 and 69) is the upper and lower blade gripping section (66 and 67). When the blade 40 is inserted into the removal instrument 50 the portion of the blade 40 just above the slot 44 is preferably perpendicular to and between the upper and lower blade gripping section (66 and 67). When the upper and lower handles (60 and 62) are squeezed together, the upper and lower blade grips (66 and 67) securely grip the portion of the blade 40 therebetween.

The upper handle 62 is immediately adjacent to the upper blade grip 67. The length of the upper handle 62 preferably extends perpendicular with respect to the upper blade protector 68. The edge of the sheet metal of the upper handle 62 is bent at an angle downward, thereby forming the upper blade flex ridge 58. The angle is preferably a right angle. At the blade gripping and flexing end 76 of the upper blade flex ridge 58, and in line with the upper blade grip 67, is an upper notch 54. When the upper handle 62 is squeezed together with a lower handle 60, the retaining member 30 of the surgical handle 20 passes through the upper notch 54, whereas the blade 40 on either side of the neck 26 is pressed downward by the upper blade flex ridge 58 on either side of the upper notch 54.

The lower handle 60 is immediately adjacent to the lower blade grip 66. The lower handle 60 preferably extends perpendicular with respect to the lower blade protector 69. The lower handle 60 is wider than the upper handle 62 and therefore the lower handle 60 extends beyond the upper handle 62. The edge of the sheet metal of the lower handle 60 is bent at an angle upward, thereby forming the lower blade flex ridge 56. The angle is preferably a right angle. At the blade gripping and flexing end 76 of the lower blade flex ridge 56 is a lower notch 52. When the upper handle 62 is squeezed together with the lower handle 60, the neck 26 of the surgical handle 20 passes into the lower notch 52 whereas the blade 40 on either side of the neck 26, is pressed upward by the lower blade flex ridge 56 on either side of the lower notch 52, as shown to advantage in FIG. 9.

To prevent the upper and lower handles (60 and 62) from squeezing beyond the desired level, a handle stop 64 may be bent at a right angle downward from the outer end of the handle end 78 of the upper handle 62. This configuration is shown in FIG. 5. In the alternative, a handle stop could be fashioned by bending an end of the lower handle 60 at an upward angle or by adding a metal or rubber piece of the appropriate size between the upper and lower handles (60 and 62). With the handle stop 64 being present, pressure between then handles 60 and 62 will first cause immediate engagement of the handle stop 64, and then force the active ends of the upper and lower handles (60 and 62) in area 76, together, to implement the blade gripping and flexing action.

FIGS. 6, 7, and 8 show the method of removing a blade 40 by using the blade removal instrument 50. FIG. 6 shows the surgical tool 80 as it is inserted into the removal instrument 50. The surgical tool 80 is positioned (as can be seen in FIG. 7 and FIG. 9) within the removal instrument 50 as follows: the neck 26 of the surgical tool 80 rests within the lower notch 52 of the lower ridge 56 of the removal instrument so that the lower ridge 56 on either side of the lower notch 52 engages the underside lower portion 49 (as shown in FIG. 1B) of a surgical blade 40; the retaining member 30 on the upper narrowed portion 28 of the surgical tool 80 is directly below the upper notch 54 in the upper ridge 58 of the removal instrument 50 so that the upper ridge 58 on either side of the upper notch 54 is directly above the middle portion of the upper side of the blade 40; and the outer end of the blade 40 rests between the upper and lower gripping sections (66 and 67).

The user squeezes the upper and lower handles (60 and 62) of the removal instrument 50 keeping his hands at a safe distance from the sharp contaminated blade 40. The correct hand position is on the handle end 78 of the removal instrument handles (60 and 62). As the handles (60 and 62) move toward each other, the removal instrument 50, as shown in FIG. 7 and FIG. 9, comes into contact with the contaminated blade 40 as follows: the blade gripping section (66 and 67) grips the upper portion of the blade 40; the upper ridge 58 surrounding the upper notch 54 pushes down on the middle section of the blade 40 surrounding the retaining member 30; and the lower ridge 56, surrounding the lower notch 52, applies pressure to the lower side of the rear portion 49 of the blade 40 on either side of the neck 26 of the surgical tool handle 20. As shown in FIG. 9, when the user applies more pressure, the rear portion 49 of the blade 40 flexes over the rear portion 34 of the retaining member 30. As shown in FIG. 8 and FIG. 9, the handle 20 of the surgical tool 80 may then be pulled away from the blade 40 while the blade 40 remains securely gripped in the gripping section (66 and 67) of the removal instrument 50.

The removal instrument 50, and the blade 40 contained therein, may then be positioned over a container appropriate for the disposal of the contaminated blade 40. The blade 40 is secured between the blade gripping section (67 and 68) and in no danger of slipping out of the removal instrument 50. Since it is enclosed both above and below by the removal instrument 50, any contaminants which drip off the blade 40 will be normally caught by the removal instrument 50. By releasing the handles (60 and 62), the blade 40 may then be allowed to fall into the disposal container. Throughout this process, the hand of the user remains safely on the handle end 78 of the removal instrument 50 and away from the sharp contaminated blade 40.

As shown in FIG. 10, the removal instrument 50 may be placed in a sterilizing container 72 containing a sanitary solution 74 to sterilize the removal instrument 50 so it may be reused. Again, the user's hands and fingers are at a safe distance from any contaminating materials, thereby removing the risk of infection.

In conclusion, it is to be understood that the present invention is not to be limited to that precisely as described hereinabove and as shown in the accompanying drawings. More specifically, variations on the invention could include, but are not limited as follows: the removal instrument may be made of different types of metal or other flexible and sanitizable material; the blade protector may be different lengths or widths to accommodate non-standard blades; the blade protector may be further enclosed by additional flaps of metal to further prevent contaminants from escaping the protector; the handle stop may be made from the upper handle, lower handle, or an additional piece of sturdy material; and the blade removal instrument may, for example, be formed of two pieces of sheet metal secured together at the location of reference numeral 70, with the instrument otherwise operating as described hereinabove. Accordingly, the present invention is not limited to the arrangements precisely as shown in the drawings and described hereinabove.

What is claimed is:

1. A sanitary surgical blade removal instrument comprising:
    a sheet metal stamping having a handle and actuation end, and a blade gripping and flexing end;
    said blade gripping and flexing end including two opposed blade gripping or engaging surfaces normally slightly spaced apart, and a pivot point formed of a folded or bent portion of said sheet metal stamping, with the sheet metal extending from said pivot point to said two opposed blade gripping surfaces, and beyond to provide two pairs of blade flexing pressure points, spaced further away from said pivot point than said blade gripping surfaces;
    said handle and actuation end including overlapping upper and lower lateral sheet metal extensions from said blade gripping and flexing end of said instrument, said extensions normally being spaced apart, having an engagement point at the outer ends thereof, and extending substantially perpendicular from said blade gripping and flexing end for a distance sufficient to permit gripping of said handle and actuation end by several fingers of the user and to provide a substantially safe distance between the fingers and a line of insertion of said blade along said blade gripping and flexing end; and
    means for gripping said blade at said opposed gripping surfaces and flexing said blade at said pressure points when said extensions are pressed together;
    whereby said blade may be removed from a surgical knife handle by shifting the knife handle away from the blade removal instrument, and the blade disposed of by releasing pressure on said extensions, without contamination of the user.

2. A sanitary surgical blade removal instrument as defined in claim 1, wherein said instrument is sterilizable.

3. A sanitary surgical blade removal instrument as defined in claim 1 wherein said instrument is formed of metal.

4. A sanitary surgical blade removal instrument as defined in claim 1 wherein said instrument is formed of stainless steel.

5. A sanitary surgical blade removal instrument as defined in claim 1 wherein said folded or bent portion is C-shaped.

6. A sanitary surgical blade removal instrument as defined in claim 1 wherein said opposed blade gripping surfaces are opposed inward indentations in the sheet metal between said pivot point and said pressure points.

7. A sanitary surgical blade removal instrument as defined in claim 1, wherein said blade has a cutting portion, a middle portion, and a handle engaging portion, said means for gripping said blade at said opposed gripping surfaces and flexing said blade at said pressure points when said extensions are pressed together comprising:
   said cutting portion being gripped between said opposed gripping surfaces;
   said middle portion being pressed downward by said upper blade flexing pressure points; and
   said handle engaging portion being flexed upward by said lower blade flexing pressure points.

8. An instrument for removing a disposable blade from a surgical tool handle, said blade having a blade slot defined therein, said tool handle having an upper narrowed portion with a neck and an elongated retaining member which engages the blade slot, said instrument comprising:
   a single sheet of material, said sheet being bent at a C-shaped fold;
   said fold connecting and separating an upper portion and a lower portion which extend generally parallel to one another;
   said upper portion including an upper blade protector, an upper blade grip, an upper instrument handle extending substantially perpendicular with respect to said upper blade protector and said upper blade grip for a distance greater than a combined length of said upper blade protector and said upper blade grip, and an upper ridge extending along an edge of said upper instrument handle, said upper ridge having an upper notch defined therein;
   said lower portion including a lower blade protector, a lower blade grip, a lower instrument handle extending beyond said upper instrument handle and extending substantially perpendicular with respect to said lower blade protector and said lower blade grip for a distance greater than a combined length of said lower blade protector and said lower blade grip, and a lower ridge extending along an edge of said lower instrument handle, said lower ridge having a lower notch defined therein; and
   said upper and lower blade protectors forming an L-shape with said upper and lower instrument handles respectively.

9. An instrument as defined in claim 8, wherein said single piece of material is sterilizable metal.

10. An instrument as defined in claim 8, wherein said single sheet of material is stainless steel.

11. An instrument for removing a disposable blade from a surgical tool handle, said blade having a blade slot defined therein, said tool handle having an upper narrowed portion with a neck and an elongated retaining member which engages the blade slot, said instrument comprising:
   a single sheet of material, said sheet being bent at a C-shaped fold;
   said fold connecting and separating an upper portion and a lower portion which extend generally parallel to one another;
   said upper portion including an upper blade protector, an upper blade grip, an upper instrument handle, and an upper ridge extending along an edge of said upper instrument handle, said upper ridge having an upper notch defined therein;
   said lower portion including a lower blade protector, a lower blade grip, a lower instrument handle extending beyond said upper instrument handle, and a lower ridge extending along an edge of said lower instrument handle, said lower ridge having a lower notch defined therein;
   said upper and lower blade protectors forming an L-shape with said upper and lower instrument handles respectively.; and
   said upper portion further including an extension at an angle, said extension preventing said upper handle and said lower handle from mating.

12. An instrument as defined in claim 11, wherein said extension is at a right angle from the bottom end of the upper instrument handle.

13. An instrument defined in claim 8, said blade has a cutting portion, a middle portion, and a handle engaging portion, said instrument having means for gripping and flexing said blade at when said upper instrument handle and said lower instrument handle are pressed together, said means for gripping and flexing comprising:
   said cutting portion being gripped between said upper blade grip and said lower blade grip;
   said middle portion being pressed downward by said upper ridge on either side of said upper notch defined by said upper ridge; and
   said handle engaging portion being flexed upward by said lower ridge on either side of said lower notch defined by said lower ridge.

14. An instrument for removing a blade having a blade slot therein from a surgical tool handle having a narrowed upper portion with a neck and a retaining member which engages the blade slot, said instrument comprising: an upper portion comprising:
   an upper blade protector;
   an upper blade grip adjacent to the upper blade protector;
   an upper instrument handle extending substantially perpendicular to said upper blade protector and said upper blade grip for a distance greater than a combined length of said upper blade protector and said upper blade grip; and
   upper pressure point means extending downward from and at an angle to said upper instrument handle, said pressure point means defining an upper notch therebetween, said upper notch being in line with said upper blade grip and said upper blade protector; a lower portion comprising:
   a lower blade protector;
   a lower blade grip adjacent to the lower blade protector;
   a lower instrument handle extending substantially perpendicular to said lower blade protector and said lower blade grip for a distance greater than a combined length of said lower blade protector and said lower blade grip, said lower instrument handle extending beyond said upper instrument handle; and lower pressure point means extending upward from, and at an angle to said lower instrument handle, said lower pressure point means defining a lower notch therebetween, said lower notch being in line with said lower blade grip and said lower blade protector;

said lower portion being substantially parallel to said upper portion; and means for flexibly connecting the upper and lower portions so that they extend essentially parallel to one another;

whereby said blade is flexed so that it may be removed from said surgical handle when said handles are pressed together.

15. An instrument a defined in claim 14, wherein said instrument is constructed from a single sheet of metal.

16. An instrument as defined in claim 15, wherein said metal is sterilizable.

17. An instrument as defined in claim 14 wherein said instrument is constructed from a single sheet of stainless steel.

18. An instrument as defined in claim 14, wherein said means for flexibly connecting the upper and lower portions is a C-shaped bend in the metal.

19. An instrument for removing a blade having a blade slot therein from a surgical tool handle having a narrowed upper portion with a neck and a retaining member which engages the blade slot, said instrument comprising: an upper portion comprising:

an upper blade protector;

an upper blade grip adjacent to the upper blade protector;

an upper instrument handle extending substantially perpendicular to said upper blade protector and said upper blade grip; and upper pressure point means extending downward from and at an angle to said upper instrument handle, said pressure point means defining an upper notch therebetween, said upper notch being in line with said upper blade grip and said upper blade protector; a lower portion comprising:

a lower blade protector;

a lower blade grip adjacent to the lower blade protector;

a lower instrument handle extending substantially perpendicular to said lower blade protector and said lower blade grip, said lower instrument handle extending beyond said upper instrument handle; and lower pressure point means extending upward from, and at an angle to said lower instrument handle, said lower pressure point means defining a lower notch therebetween, said lower notch being in line with said lower blade grip and said lower blade protector;

said lower portion being substantially parallel to said upper portion;

means for flexibly connecting the upper and lower portions so that they extend essentially parallel to one another; and a handle stop located between the ends of said handles located away from said blade grip and said blade protector;

whereby said blade is flexed so that it may be removed from said surgical handle when said handles are pressed together.

* * * * *